United States Patent
Kim

(10) Patent No.: US 10,286,187 B2
(45) Date of Patent: May 14, 2019

(54) SAFE CATHETER

(71) Applicant: MEDIFIRST CO., LTD., Chungcheongnam-do (KR)

(72) Inventor: Keun Shik Kim, Chungcheongnam-do (KR)

(73) Assignee: MEDIFIRST CO., LTD., Chungcheongnam-do (KR)

( * ) Notice: Subject to any disclaimer, the term of this patent is extended or adjusted under 35 U.S.C. 154(b) by 254 days.

(21) Appl. No.: 15/119,075

(22) PCT Filed: Feb. 24, 2015

(86) PCT No.: PCT/KR2015/001735
§ 371 (c)(1),
(2) Date: Aug. 15, 2016

(87) PCT Pub. No.: WO2015/126218
PCT Pub. Date: Aug. 27, 2015

(65) Prior Publication Data
US 2017/0049999 A1 Feb. 23, 2017

(30) Foreign Application Priority Data

Feb. 24, 2014 (KR) .................... 10-2014-0021618
Nov. 7, 2014 (KR) .................... 10-2014-0154250

(51) Int. Cl.
*A61M 25/06* (2006.01)

(52) U.S. Cl.
CPC .............................. *A61M 25/0631* (2013.01)

(58) Field of Classification Search
CPC .......... A61M 25/0606; A61M 25/0631; A61M 25/0681
See application file for complete search history.

(56) References Cited

U.S. PATENT DOCUMENTS 5,713,876 A    2/1998  Bogert et al.
6,942,642 B2   9/2005  Suzuki
(Continued)

FOREIGN PATENT DOCUMENTS

EP    1331018      7/2003
JP    10-04403     2/1998
(Continued)

OTHER PUBLICATIONS

Office Action dated Jul. 25, 2017 corresponding to Japanese Application No. 2016-570751, 3 pages.
(Continued)

*Primary Examiner* — Nathan R Price
*Assistant Examiner* — Melissa A Snyder

(57) ABSTRACT

Provided is a catheter, which can protect a medical personnel and a patient from a needle stick injury when it is disposed of after use. In an example embodiment, the catheter includes a needle, a plug having a front end coupled to the needle, a first case formed to enclose the needle, a socket coupled to a front end of the first case, a gear vertically coupling the first case and the socket to each other and having a tooth formed on an outer periphery of one side and a needle groove formed therein to allow the needle to pass therethrough, a catheter hub fastened by the tooth of the gear, and a tube coupled to the front end of the catheter hub.

20 Claims, 5 Drawing Sheets

(56) References Cited

U.S. PATENT DOCUMENTS

| | | |
|---|---|---|
| 8,226,612 B2 | 7/2012 | Nakajima |
| 2004/0044310 A1 | 3/2004 | Suzuki |
| 2004/0122373 A1 | 6/2004 | Botich et al. |
| 2006/0106335 A1* | 5/2006 | Putter .................. A61M 5/158 604/93.01 |
| 2007/0255221 A1* | 11/2007 | Nakajima ......... A61M 25/0017 604/168.01 |
| 2008/0319387 A1* | 12/2008 | Amisar .............. A61M 25/0111 604/95.04 |

FOREIGN PATENT DOCUMENTS

| | | |
|---|---|---|
| JP | 2001-522658 | 11/2001 |
| JP | 2003-093506 | 4/2003 |
| JP | 2006-296797 | 11/2006 |
| JP | 2007-296022 | 11/2007 |
| KR | 10-2000-0073531 | 12/2000 |
| RU | 2170593 | 7/2001 |

OTHER PUBLICATIONS

International Search Report dated May 1, 2015 for PCT/KR2015/001735.
Office Action dated Nov. 29, 2017 corresponding to Russian Patent Application No. 2016137320 with English translation, 18 pages.

* cited by examiner

[Fig. 1]
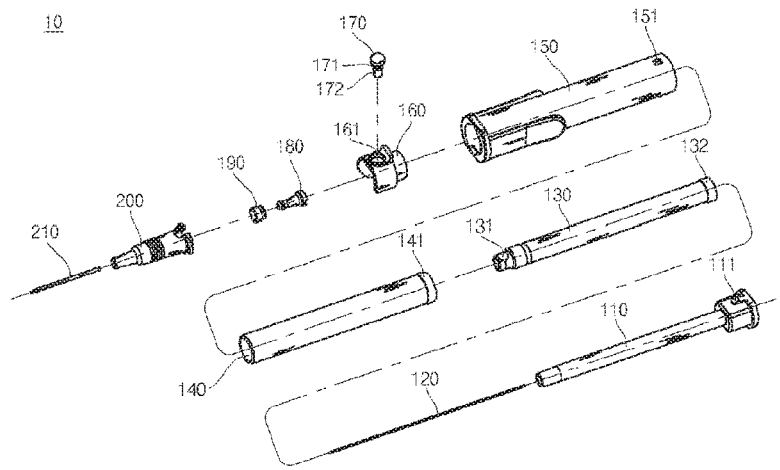
[Fig. 2]
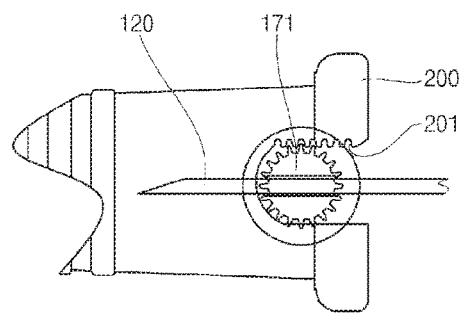
[Fig. 3]
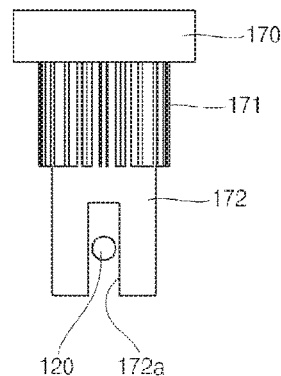
[Fig. 4]
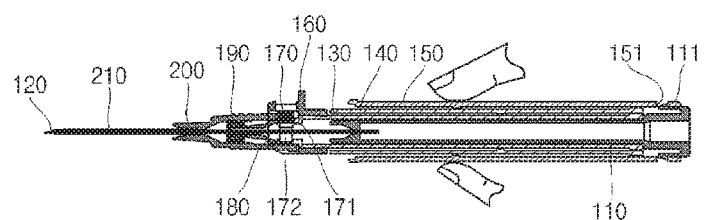

[Fig. 5]
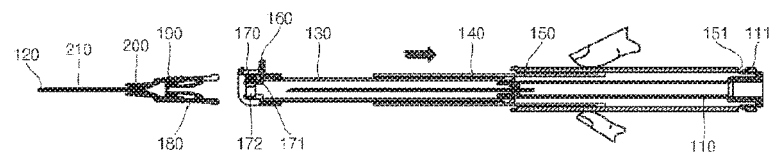
[Fig. 6]
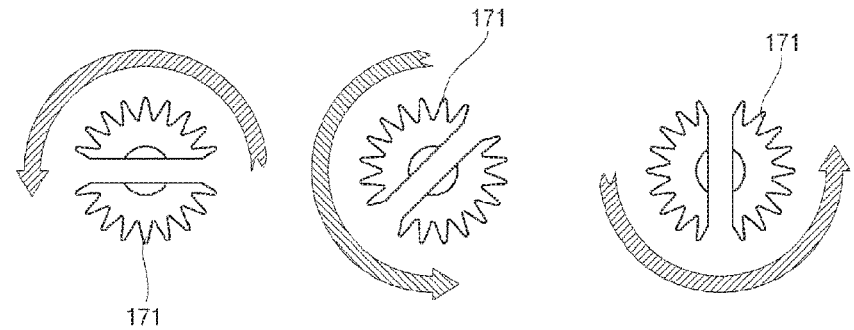
[Fig. 7]
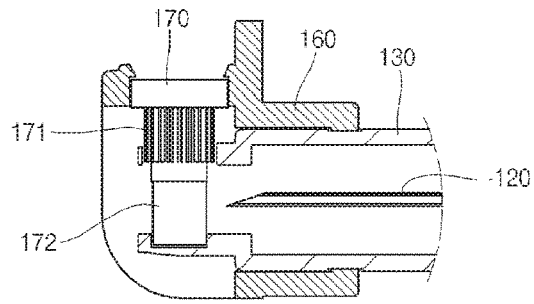
[Fig. 8]
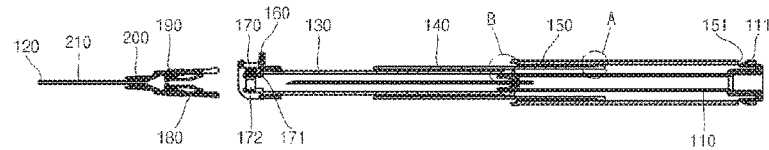
[Fig. 9]
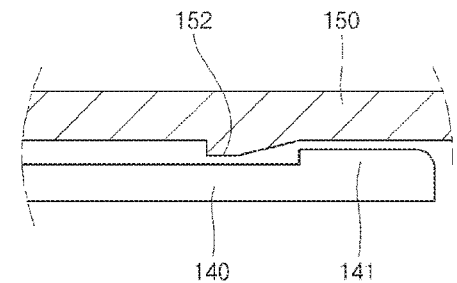

[Fig. 10]
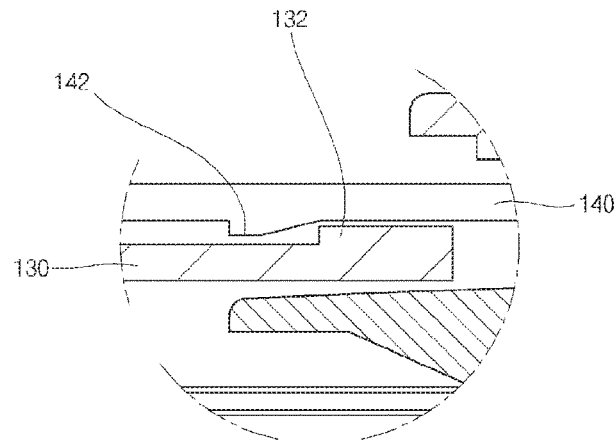
[Fig. 11]
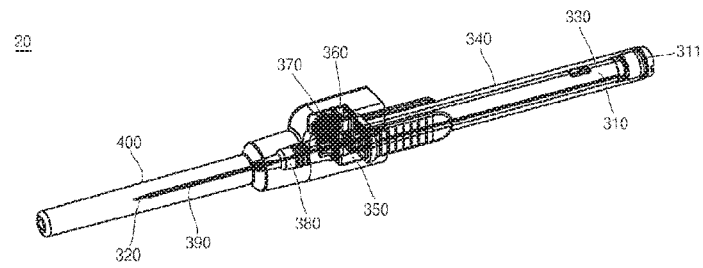
[Fig. 12]
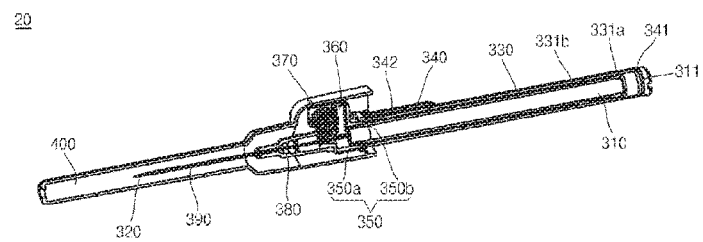
[Fig. 13]
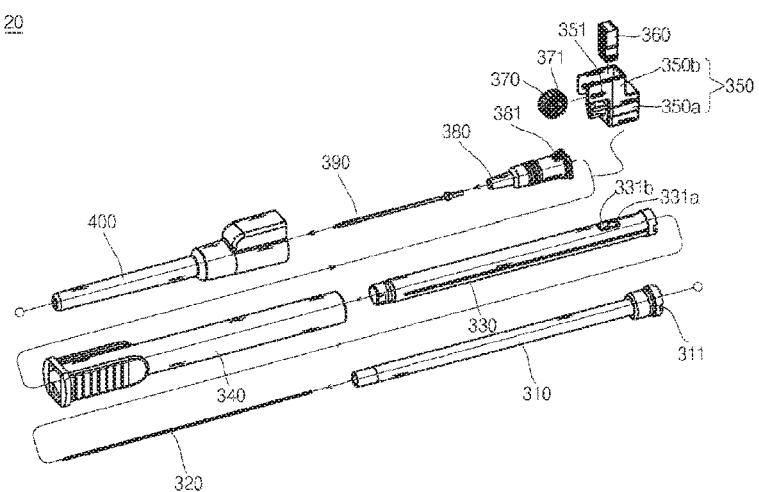

[Fig. 14]
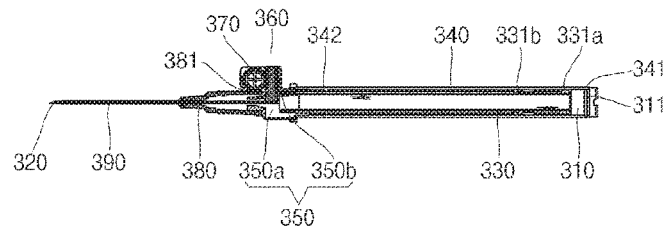
[Fig. 15]
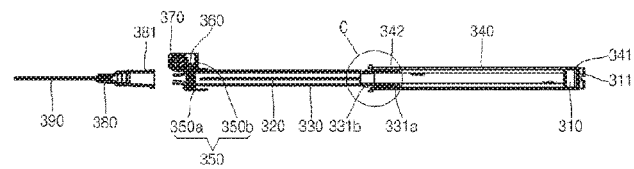
[Fig. 16]
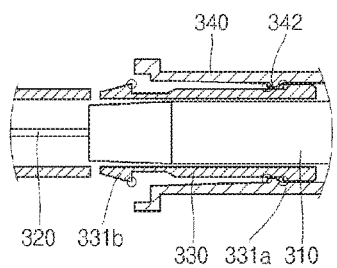
[Fig. 17]
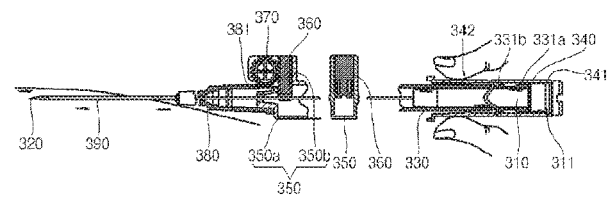
[Fig. 18]
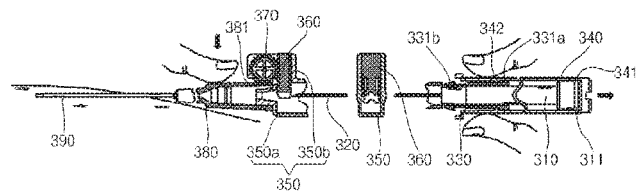
[Fig. 19]
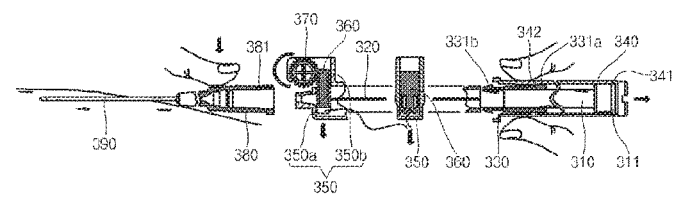

[Fig. 20]
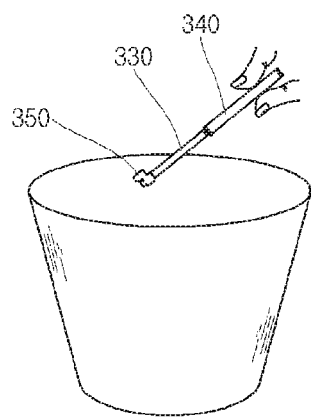

SAFE CATHETER

This application claims the priority of Korean Patent Application Nos. 10-2014-0021618, and 10-2014-0154250, filed on Feb. 24, 2014, and Nov. 7, 2014 in the KIPO (Korean Intellectual Property Office), the disclosure of which is incorporated herein entirely by reference. Further, this application is the National Stage application of International Application No. PCT/KR2015/001735, filed Feb. 24, 2015, which designates the United States and was published in Korean. Each of these applications is hereby incorporated by reference in their entirety into the present application.

TECHNICAL FIELD

The present invention relates to a catheter, which can protect a medical personnel and a patient from a needle stick injury when it is disposed of after use.

BACKGROUND ART

Catheters are effective infusion devices for administer medical fluids or drugs to patients and are widely used in hospitals. A catheter is typically configured to leave a hub having a tube formed at a front end in the body of a patient requiring frequent drug infusion and providing the convenience of eliminating the need for the needle to newly puncture the skin of the patient for the purpose of additionally infusing the medical fluids or drugs.

In order to insert a tube into the body of a patient, the catheter is configured such that the tube through which a needle initially passes is inserted into the body of the patient and only the needle is then retracted for removal.

However, in the course of removing the needle, the medical personnel or the patient may be subjected to the risk of a needle stick injury, resulting in infection from the needle. Accordingly, a highly careful use of the needle is required.

DISCLOSURE OF THE INVENTION

Technical Problem

Embodiments of the present invention provide a catheter, which can protect a medical personnel and a patient from a needle stick injury when it is disposed of after use.

Technical Solution

According to an aspect of the present invention, there is provided a catheter including a needle, a plug having a front end coupled to the needle, a first case formed to enclose the needle, a socket coupled to a front end of the first case, a gear vertically coupling the first case and the socket to each other and having a tooth formed on an outer periphery of one side and a needle groove formed therein to allow the needle to pass therethrough, a catheter hub fastened by the tooth of the gear, and a tube coupled to the front end of the catheter hub.

Here, the tooth may be formed at an upper portion of the gear and the needle groove may be formed at a lower portion of the gear.

The socket and the first case may be integrally coupled to each other by the gear.

The needle may be separated from the needle groove of the gear in a lengthwise direction of the first case.

After the needle is separated, the gear may rotate along the gear groove of the catheter hub.

In addition, the socket and the first case may be separated from the catheter hub according to the rotation of the gear.

After the needle is separated from the gear, the catheter may be accommodated within the first case.

The catheter may further include a second case enclosing the outer periphery of the first case and formed such that a front end of a throughhole has a smaller diameter than a front end of the first case.

The catheter may further include a needle hub integrally coupled to the plug through a protrusion of the plug, enclosing the outer periphery of the second case and formed such that a front end of a throughhole has a smaller diameter than a front end of the second case.

In addition, the needle hub, the second case and the first case may be sequentially retracted in that order.

According to another aspect of the present invention, there is provided a catheter including a needle, a plug having a front end coupled to the needle, a moving bar coupled to an outer periphery of the plug, a pivot integrally coupled to a front end of the moving bar and including a first region through which the needle disposed at its lower portion passes and a second region protruding to an upper portion of the first region, a rack supported by the needle and positioned at a rear end of the second region, a gear coupled to be engaged with the rack at a front end of the second region, a hub coupled to a front end of the pivot and including a tooth meshed with the gear, and a tube coupled to a front end of the hub.

Here, the plug may be outwardly retracted within the moving bar in a lengthwise direction of the moving bar.

The needle may be positioned within the moving bar while being retracted

The rear end of the first region may be connected to the moving bar and a front end of the first region may be inserted into the hub.

The rack may be positioned on an upper region between the front end of the moving bar and the rear end of the hub.

The gear may be fixed by being engaged with the rack and the tooth of the hub to then couple the pivot and the hub to each other.

When the needle is retracted, the rack may be lowered from the second region to the first region.

As the rack is lowered, the gear may be rotated to then be disengaged from the tooth of the hub and the pivot and the hub may be separated from each other.

The rack may cut off an outwardly traveling path of the needle extending from the pivot.

The catheter may further include a needle hub enclosing the outer periphery of the moving bar and having a rear end integrally coupled to the rear end of the plug.

Advantageous Effects

As described above, the catheter according to the present invention includes a gear groove formed in a catheter hub, a socket and a first case provided to be coupled to the catheter hub through a gear, and a groove formed at a bottom end of the gear to allow a needle to pass therethrough, thereby safely protecting a patient and medical personnel from a needle stick injury without exposing the needle by allowing the gear to rotate only when the needle is retracted and enclosed by the first case to separate the socket and the first case from the catheter hub.

In addition, in the catheter according to the present invention, the hub and the moving bar are engaged or disengaged by the teeth formed in the gear, the rack and the hub, the rack cuts off an outwardly traveling path of the needle after the needle is retracted to separate the moving bar and the hub from each other, thereby safely protecting a patient and medical personnel from a needle stick injury without exposing the needle.

BRIEF DESCRIPTION OF THE DRAWINGS

FIG. 1 is an exploded perspective view of a catheter according to an embodiment of the present invention;

FIG. 2 is a plan view illustrating a state in which a needle is engaged with a holder of the catheter according to an embodiment of the present invention;

FIG. 3 is a front view illustrating a state in which a needle is engaged with a gear of the catheter according to an embodiment of the present invention;

FIGS. 4 and 5 illustrate a procedure in which a needle hub is separated from a catheter hub of the catheter according to an embodiment of the present invention;

FIGS. 6 and 7 illustrate a procedure in which a gear of the catheter according to an embodiment of the present invention is rotated and a needle is separated from a catheter hub;

FIG. 8 illustrates a state in which a needle is separated from a catheter hub of the catheter according to an embodiment of the present invention;

FIG. 9 is a partially enlarged view illustrating a portion 'A' of FIG. 8;

FIG. 10 is a partially enlarged view illustrating a portion 'B' of FIG. 8;

FIGS. 11 and 12 are perspective views of a catheter according to another embodiment of the present invention;

FIG. 13 is an exploded perspective view of a catheter according to another embodiment of the present invention;

FIGS. 14 and 15 illustrate a procedure in which a needle hub is separated from a catheter hub of the catheter according to another embodiment of the present invention;

FIG. 16 is an enlarged sectional view illustrating a portion 'C' of FIG. 15; and FIGS. 17 to 20 illustrate an operation procedure of a catheter according to another embodiment of the present invention.

MODE FOR CARRYING OUT THE INVENTION

Hereinafter, examples of embodiments of the invention will be described in detail with reference to the accompanying drawings such that they can easily be made and used by those skilled in the art.

Hereinafter, a catheter according to an embodiment of the present invention will be described.

FIG. 1 is an exploded perspective view of a catheter according to an embodiment of the present invention, FIG. 2 is a plan view illustrating a state in which a needle is engaged with a holder of the catheter according to an embodiment of the present invention, FIG. 3 is a front view illustrating a state in which a needle is engaged with a gear of the catheter according to an embodiment of the present invention, FIGS. 4 and 5 illustrate a procedure in which a needle hub is separated from a catheter hub of the catheter according to an embodiment of the present invention, FIGS. 6 and 7 illustrate a procedure in which a gear of the catheter according to an embodiment of the present invention is rotated and a needle is separated from a catheter hub, FIG. 8 illustrates a state in which a needle is separated from a catheter hub of the catheter according to an embodiment of the present invention, FIG. 9 is a partially enlarged view illustrating a portion 'A' of FIG. 8, and FIG. 10 is a partially enlarged view illustrating a portion 'B' of FIG. 8.

Referring to FIGS. 1 to 10, the catheter 10 according to an embodiment of the present invention includes a plug 110, a needle 120, a first case 130, a second case 140, a needle hub 150, a socket 160, a gear 170, a holder 180, a gasket 190, a catheter hub 200, and a tube 210.

The plug 110 has one end coupled to the needle 120. The plug 110 supports the needle 120 to allow the needle 120 to be inserted into the body of a patient or to be retracted and removed after being inserted. The plug 110 includes a protrusion 111 formed at the other end of the plug 110 to then be coupled to the needle hub 150 through the protrusion 111. Therefore, when the medical personnel grasps the needle hub 150 to use the catheter 10 according to an embodiment of the present invention, the plug 110 may be retracted together with the needle hub 150 and a front end of the needle 120 may also be retracted, which will later be described.

The needle 120 has a hollow and its front end is sharply formed to puncture the skin of the patient. A rear end of the needle 120 is coupled to the plug 110, so that the needle 120 can be securely inserted into the body of the patient together with the tube 210. In addition, once the tube 210 is inserted into the body of the patient, the needle 120 is retracted along the plug 110 to allow only the tube 210 to remain in the body of the patient. In addition, as will be described, since the front end of the needle 120 is enclosed and concealed by the first case 130 and the second case 140, it is possible to safely prevent the medical personnel or the patient from being pricked by the front end of the needle 120.

The first case 130 is coupled to the plug 110. In more detail, a throughhole having a larger diameter than the plug 110 is formed in the first case 130, the needle 120 and the plug 110 are inserted into the throughhole, and the first case 130 is coupled to the outer periphery of the plug 110.

In addition, a gear hole 131 is formed in the front of the first case 130 to provide a region into which the gear 170 is inserted. The gear 170 coupled to the socket 160 is inserted into the gear hole 131, thereby maintaining a front end of the first case 130 to be in a state in which it is coupled to the socket 160. Therefore, when the first case 130 is retracted, the socket 160 can be easily separated from the catheter hub 200 along the first case 130 by a medical personnel.

In addition, a protrusion 132 is formed at a rear end of the first case 130. The protrusion 132 has a larger diameter than the other region of the first case 130. In addition, the diameter of the protrusion 132 is larger than that of the throughhole formed at the front end of the second case 140. Therefore, if the needle hub 150 is retracted in a state in which the medical personnel grasps the needle hub 150, so that the second case 140 is retracted, the protrusion 132 of the first case 130 is locked on the front end of the second case 140, thereby sequentially performing the operation of retracting the first case 130.

The second case 140 has a throughhole having a larger diameter than the first case 140, so that the first case 140 is inserted into the throughhole and the second case 140 is coupled to the outer periphery of the first case 130. As described above, the front end of the second case 140 is smaller than the protrusion 132 formed at the rear end of the first case 130. Thus, if the second case 140 is retracted, the protrusion 132 of the first case 130 is locked, so that the first case 130 may also be retracted.

In addition, a protrusion 142 is formed at the rear end of the second case 140 and has a larger diameter than the front end of the needle hub 150. Therefore, if medical personnel retracts the needle hub 150 in a state in which the needle hub 150 is grasped, the protrusion 142 of the second case 140 is locked on the front end of the needle hub 150, thereby allowing the second case 140 to perform a retracting operation.

The needle hub 150 has a throughhole formed therein to enclose the outer periphery in a state in which the second case 140 is inserted into the throughhole. A coupling hole 151 is formed at the rear end of the needle hub 150 to then be coupled to the protrusion 111 of the plug 110. Therefore, the needle hub 150 is maintained in a state in which it is integrally coupled to the plug 110. In the catheter 10 according to an embodiment of the present invention, the needle hub 150 is a portion grasped by the hand of the medical personnel and performs operations of inserting the needle 120 into the body of the patient and retracting the needle 120 after being inserted. If the medical personnel retracts the needle hub 150, the second case 140 is retracted, so that the first case 130 is then retracted, thereby retracting the needle 120 in a state in which the needle 120 is enclosed by the first case 130. Therefore, since a tip of the needle 120 is not exposed, both of the medical personnel and the patient can be safely protected from a needle stick injury.

The socket 160 is coupled to the front end of the first case 130. The socket 160 also has a gear hole 161 formed at a corresponding location of the gear hole 131 of the first case 130. The gear 170 is coupled to the socket 160 from above through the gear hole 161. The socket 160 may be integrally formed with the first case 130 through the gear 170.

The gear 170 is sequentially coupled to the gear hole 161 of the socket 160 and the gear hole 131 of the first case 130. The gear 170 has a tooth 171 formed at its upper portion and a needle hole 172a formed at its bottom end to allow the needle 120 to pass therethrough. Since the gear 170 is coupled to the needle hole 172a in a state in which the needle 120 passes through the needle hole 172a, the gear 170 is not rotated until the needle 120 is retracted and removed away. Therefore, since the gear 170 is rotated only after the tip of the needle 120 is enclosed by the first case 130, it is possible to fundamentally protect the medical personnel or the patient from a needle stick injury due to the exposure of the needle 120.

Then, after the needle 120 is retracted by the plug 110, the gear 170 freely rotates, thereby separating the gear 170 from the catheter hub 200. Accordingly, the socket 160 and the first case 130 are separated from the catheter hub 200, thereby leaving only the catheter hub 200 in the body of the patient.

The holder 180 allows the needle 120 to pass therethrough. The holder 180 appropriately maintains the position and retracting direction of the needle 120.

The gasket 190 fixedly supports the holder 180 within the catheter hub 200 and prevents medical fluids from leaking out from the catheter hub 200. Alternatively, the gasket 190 may also be integrally formed with the holder 180 according to the choice made by one skilled in the art.

The catheter hub 200 is coupled to the socket 160 by the gear 170. The catheter hub 200 includes a gear groove 201 formed in its upper portion. Therefore, the tooth of the gear 170 is induced to rotate along the gear groove 201. As the gear 170 rotates, the catheter hub 200 is disengaged from the gear 170 and is then separated from the socket 160 and the first case 130 accordingly.

The tube 210 is coupled to the catheter hub 200. The tube 210 has a throughhole formed therein to accommodate the needle 120. The tube 210 is inserted into the body of the patient together with the needle 120, and after the needle 120 is retracted and removed away, only the tube 210 is left in the body of the patient. Therefore, when another medical fluid is injected into the catheter hub 200 using an injector, etc., the medical fluid is infused through the tube 210.

As described above, in the catheter 10 according to an embodiment of the present invention, the gear groove 201 is provided in the catheter hub 200, the socket 160 and the first case 130 are provided to be coupled to the catheter hub 200 through the gear 170, and the needle hole 172a is provided at the bottom end of the gear 170 to allow the needle 120 to pass therethrough. Thus, the needle 120 is retracted and the gear 170 rotates only after it is enclosed by the first case 130, so that the socket 160 and the first case 130 are separated from the catheter hub 200, thereby safely protecting a patient and medical personnel from a needle stick injury without exposing the needle 120.

Hereinafter, a catheter according to another embodiment of the present invention will be described.

FIGS. 11 and 12 are perspective views of a catheter according to another embodiment of the present invention, FIG. 13 is an exploded perspective view of a catheter according to another embodiment of the present invention, FIGS. 14 and 15 illustrate a procedure in which a needle hub is separated from a catheter hub of the catheter according to another embodiment of the present invention, and FIG. 16 is an enlarged sectional view illustrating a portion 'C' of FIG. 15.

Referring to FIGS. 11 to 16, the catheter 20 according to another embodiment of the present invention includes a plug 310, a needle 320, a moving bar 330, a needle hub 340, a pivot 350, a rack 360, a gear 370, a hub 380, a tube 390 and a cap 400.

The plug 310 has one end coupled to the needle 320. The plug 310 supports the needle 320 to allow the needle 320 to be inserted into the body of a patient or to be retracted and removed after being inserted. The plug 310 includes a protrusion 311 formed at the other end of the plug 310 to then be integrally coupled to the needle hub 340 through the protrusion 311. Therefore, when the medical personnel grasps the needle hub 340 to use the catheter 20 according to another embodiment of the present invention, the plug 310 may be retracted together with the needle hub 340 and the needle 320 may also be retracted.

The needle 320 has a hollow and its front end is sharply formed to puncture the skin of the patient. A rear end of the needle 320 is coupled to one end of the plug 310, so that the needle 320 can be securely inserted into the body of the patient together with the tube 390. In addition, once the tube 390 is inserted into the body of the patient, the needle 320 is retracted along the plug 310 to allow only the tube 390 to remain in the body of the patient. Here, since the front end of the needle 320 is enclosed and concealed in the moving bar 330, it is possible to safely prevent the medical personnel or the patient from being pricked by the front end of the needle 320.

The moving bar 330 is coupled to the plug 310. In more detail, a throughhole having a larger diameter than the plug 310 is formed in the moving bar 330, the plug 310 is inserted into the throughhole. That is to say, the moving bar 330 is coupled to the outer periphery of the plug 310. In addition, the pivot 350 is integrally coupled to one end of the moving bar 330, which will later be described.

Meanwhile, a first locking ledge 331a and a second locking ledge 331b are formed at a rear end of the moving bar 330. A locking hook 342 of the needle hub 340 is locked on the first and second locking ledges 331a and 331b when the needle hub 340 is retracted, which will later be described. Accordingly, when the plug 310 and the needle hub 340 are retracted, the moving bar 330 and the needle hub 340 are not completely separated from each other and the needle 320 is securely positioned within the moving bar 330.

The needle hub 340 includes a throughhole formed therein to enclose its outer periphery in a state in which the moving bar 330 is inserted into the throughhole. The needle hub 340 has a groove 341 formed at an inner periphery of its rear end to be coupled to the protrusion 311 of the plug 310. Therefore, the needle hub 340 is maintained in a state in which it is integrally coupled to the plug 310. In the catheter 20 according to another embodiment of the present invention, the needle hub 340 is a portion grasped by the hand of the medical personnel and performs operations of inserting the needle 320 into the body of the patient and retracting the needle 320 after being inserted. If the medical personnel retracts the needle hub 340, the plug 310 integrally coupled to the needle hub 340 is retracted together with the needle hub 340, and the needle 320 fixed at one end of the plug 310 is also retracted. Here, since the needle 320 is retracted in a state in which it is enclosed by the moving bar 330, a tip of the needle 320 is not exposed to the outside. Therefore, both of the medical personnel and the patient can be safely protected from the needle stick injury.

Meanwhile, the needle hub 340 has a locking hook 342 formed at an inner periphery of its front end to be locked on the first and second locking ledges 331a and 331b of the moving bar 330. Therefore, when the needle hub 340 is retracted, the locking hook 342 is locked on the first locking ledge 331a and is not retracted any longer, so that the moving bar 330 and the needle hub 340 are not completely separated from each other and the needle 320 is securely positioned within the moving bar 330. In addition, even if the needle hub 340 moves toward its front end after the retracting of the needle hub 340 is completed, the locking hook 342 is locked on the second locking ledge 331b and is not moved forward any longer, so that the needle 320 is securely positioned within the moving bar 330 without outwardly protruding from the moving bar 330.

The pivot 350 is integrally coupled to a front end of the moving bar 330. In addition, the front end of the pivot 350 is inserted into the hub 380, which will later be described. The pivot 350 includes a first region 350a through which the needle 320 passes and a second region 350b in which the rack 360 and the gear 370 are mounted. Here, the first region 350a is a region coupled to the moving bar 330 and the hub 380 disposed under the pivot 350, and the second region 350b is a region upwardly protruding from the first region 350a. Meanwhile, a coupling hole 352 may further be formed at a front end of the second region 350b to be coupled to the gear 370.

The rack 360 is positioned in the second region 350b of the pivot 350. In particular, the rack 360 may be positioned at a rear end of the second region 350b. In addition, the rack 360 may be positioned between the plug 310 and the hub 380, which will later be described. Here, the rack 360 is supported by the needle 320 coupled thereto while passing through the first region 350a of the pivot 350 and is positioned in the second region 350b. Therefore, when the needle 320 is retracted, the rack 360 is lowered from the second region 350b disposed on the pivot 350 to the first region 350a disposed under the pivot 350. Since the rack 360 is lowered to be positioned in the first region 350a, thereby preventing the needle 320 from being exposed to the outside of the pivot 350. In other words, since a path extending toward the outside of the pivot 350 is cut off by the rack 360, the needle 320 can be securely positioned within the moving bar 330. Therefore, since the tip of the needle 320 is not exposed, both of the medical personnel and the patient can be safely protected from the needle stick injury.

Meanwhile, the rack 360 has a tooth formed to be engaged with the gear 370, which will later be described. In more detail, the rack 360 may have the tooth formed at its front end facing the gear 370. In addition, the tooth may also be formed at a rear end of the rack 360 facing the front end of the rack 360. The gear 370 is induced to rotate along the tooth.

The gear 370 is positioned at the front end second region 350b of the pivot 350. The gear 370 is coupled to the coupling hole 351 of the second region 350b to then be fixed to the second region 350b. Here, the gear 370 may further include a coupling protrusion 371 to be coupled to the coupling hole 351. Meanwhile, the gear 370 is mounted on a top end of the hub 380, which will later be described. In addition, a tooth 381 is formed on the top end of the hub 380 on which the gear 370 is mounted to be engaged with the gear 370. Further, the gear 370 is fixed to be engaged with the rack 360 positioned at the rear end of the second region 350b. That is to say, the rack 360, the gear 370 and the hub 380 are fixedly engaged with one another by the respective teeth formed therein.

In addition, when the needle 320 is retracted, the rack 360 is lowered, and the gear 370 engaged with the rack 360 is rotated to be disengaged from the tooth 381 of the hub 380. Therefore, the pivot 360 and the needle hub 340 are separated from the hub 380, so that only the hub 380 is left in the body of the patient.

The hub 380 is coupled to the front end of the first region 350a of the pivot 350. In more detail, the front end of the first region 350a may be inserted into a rear end of the hub 380. In addition, the tooth 381 corresponding to the gear 370 is formed on a rear end of the hub 380. The hub 380 is coupled to the pivot 350 by the gear 370 engaged with the tooth 381.

Before the catheter 20 is used, the gear 370 mounted on the tooth 381 is engaged with the tooth 381 to be fixed thereto. When the needle 320 is retracted after the catheter 20 is used, the rack 360 may be lowered and the gear 370 is disengaged from the tooth 381, thereby separating the hub 380 and the pivot 350 from each other.

The tube 390 is coupled to the front end of the hub 380. The tube 390 has a throughhole formed therein to accommodate the needle 320. The tube 390 is inserted into the body of the patient together with the needle 320, and after the needle 320 is retracted and removed away, only the tube 390 is left in the body of the patient. Therefore, when another medical fluid is injected into the hub 380 using an injector, etc., the medical fluid is infused through the tube 390.

The cap 400 is coupled to the catheter hub 340 before the needle 320 is inserted into the body of the patient, so that the tip of the needle 320 may not be exposed. Then, the cap 400 is separated and removed when the needle 320 is inserted into the body of the patient.

FIGS. 17 to 20 illustrate an operation procedure of a catheter according to another embodiment of the present invention.

First, referring to FIG. 17, a medical personnel grasps a needle hub 340 by the hand and inserts a needle 320 and a tube 390 into the body of a patient. Here, a moving bar 330 is inserted into the needle hub 340 and a plug 310 is inserted into the moving bar 330. Here, rear ends of the needle hub 340 and the plug 310 are fixed to be integrally coupled with each other. In addition, a rack 360, a gear 370 and a tooth 381 of a hub 380 are fixedly engaged with one another. Here, the rack 360 is supported by the needle 320 passing through a first region 350a of a pivot 350 to be positioned in a second region 350b of the pivot 350.

Referring to FIG. 18, in order to leave only the tube 390 in the body of the patient, the medical personnel pulls back the needle hub 340 while pressing the hub 380 by another hand. Therefore, the needle hub 340 is retracted along the outer and inner peripheries of the moving bar 330 positioned between the needle hub 340 and the plug 310. Here, since the needle 320 is coupled to the plug 310, the needle 320 is also retracted at the same time when the plug 310 is retracted. Then, the retracted needle 320 is positioned within the moving bar 330.

Meanwhile, a first locking ledge 331a and a second locking ledge 331b are formed at a rear end of the moving bar 330 and a locking hook 342 is formed on an inner periphery of a front end of the needle hub 340. Accordingly, when the needle hub 340 is retracted, the locking hook 342 is locked on the first and second locking ledges 331a and 331b and is prevented from being retracted or moved forward any longer. That is to say, the needle hub 340 is not retracted any longer by the first locking ledge 331a and is prevented from being separated from the moving bar 330, so that the needle 320 can be securely positioned within the moving bar 330 without being exposed to the outside. In addition, the needle hub 340 is prevented from moving forward by the second locking ledge 331b, so that the needle 320 is securely positioned within the moving bar 330 without being exposed to the outside.

Referring to FIG. 19, as the needle 32 is retracted, the rack 360, which is positioned in the second region 350b of the pivot 350 while being supported by the needle 320, is lowered to the first region 350a. As the rack 360 is lowered, the gear 370 is rotated counterclockwise and is disengaged from the tooth 381 according to the rotation of the rack 360, thereby separating the pivot 350 and the hub 380 from each other. Therefore, only the tube 390 and the hub 380 are left in the body of the patient. In addition, since the rack 360 cuts off a path of the pivot 350 extending toward the outside, the separated needle 320 may not outwardly protrude but may be securely positioned within the moving bar 330. Therefore, since a tip of the needle 320 is not exposed, both of the medical personnel and the patient can be safely protected from the needle stick injury.

Referring to FIG. 20, components of the catheter 20 separated after use, other than the tube 390 and the hub 380, are disposed of into a medical waste bin.

As described above, the catheter 20 according to another embodiment of the present invention includes the pivot 350 provided between the moving bar 330 and the hub 380 to allow the rack 360 and the gear 370 to be mounted thereon, and the rack 360, the gear 370 and the tooth 381 of the hub 380 are engaged with one another to be fixedly coupled to one another. Here, the pivot 350 and the moving bar 330 are integrally coupled to each other. In addition, the rack 360 is supported by the needle 320 passing through the first region 350a disposed under the pivot 350 to then be positioned in the second region 350b of the pivot 350. In addition, when the needle 320 is retracted, the rack 360 is lowered from the second region 350b to the first region 350a and the gear 370 is rotated to be disengaged from the tooth 381, thereby separating the hub 380 and the pivot 350 from each other. At the same time, the path extending from the moving bar 330 to the pivot 350 is cut off by the rack 360, thereby allowing the needle 320 to be securely positioned within the moving bar 330. Therefore, the needle 320 is not exposed to the outside, thereby safely protecting the patient and the medical personnel from the needle stick injury.

While the safe catheter according to the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

In the catheter according to the present invention, a gear groove is formed in a catheter hub, a socket and a first case provided to be coupled to the catheter hub through a gear, and a groove formed at a bottom end of the gear to allow a needle to pass therethrough, thereby safely protecting a patient and medical personnel from a needle stick injury without exposing the needle by allowing the gear to rotate only when the needle is retracted and enclosed by the first case to separate the socket and the first case from the catheter hub.

In addition, in the catheter according to the present invention, the hub and the moving bar are engaged or disengaged by the teeth formed in the gear, the rack and the hub, the rack cuts off an outwardly traveling path of the needle after the needle is retracted to separate the moving bar and the hub from each other, thereby safely protecting a patient and medical personnel from a needle stick injury without exposing the needle.

The invention claimed is:

1. A catheter comprising:
   a needle;
   a plug having a front end coupled to the needle;
   a first case formed to enclose the needle;
   a socket coupled to a front end of the first case;
   a gear vertically coupling the first case and the socket to each other and having a tooth formed on an outer periphery of one side and a needle groove formed therein to allow the needle to pass therethrough;
   a catheter hub fastened by the tooth of the gear; and
   a tube coupled to the front end of the catheter hub.

2. The catheter of claim 1, wherein the tooth is formed at an upper portion of the gear and the needle groove is formed at a lower portion of the gear.

3. The catheter of claim 1, wherein the socket and the first case are integrally coupled to each other by the gear.

4. The catheter of claim 1, wherein the needle is separated from the needle groove of the gear in a lengthwise direction of the first case.

5. The catheter of claim 1, wherein after the needle is separated, the gear rotates along the gear groove of the catheter hub.

6. The catheter of claim 5, wherein the socket and the first case are separated from the catheter hub according to the rotation of the gear.

7. The catheter of claim 1, wherein after the needle is separated from the gear, the catheter is accommodated within the first case.

8. The catheter of claim 1, further comprising a second case enclosing the outer periphery of the first case and formed such that a front end of a throughhole has a smaller diameter than a front end of the first case.

9. The catheter of claim 8, further comprising a needle hub integrally coupled to the plug through a protrusion of the plug, enclosing the outer periphery of the second case and formed such that a front end of a throughhole has a smaller diameter than a front end of the second case.

10. The catheter of claim 8, wherein the needle hub, the second case and the first case are sequentially retracted in that order.

11. A catheter comprising:
a needle;
a plug having a front end coupled to the needle;
a moving bar coupled to an outer periphery of the plug;
a pivot integrally coupled to a front end of the moving bar and including a first region through which the needle disposed at its lower portion passes and a second region protruding to an upper portion of the first region;
a rack supported by the needle and positioned at a rear end of the second region;
a gear coupled to be engaged with the rack at a front end of the second region;
a hub coupled to a front end of the pivot and including a tooth meshed with the gear; and
a tube coupled to a front end of the hub.

12. The catheter of claim 11, wherein the plug is outwardly retracted within the moving bar in a lengthwise direction of the moving bar.

13. The catheter of claim 11, wherein the needle is positioned within the moving bar while being retracted.

14. The catheter of claim 11, wherein the rear end of the first region is connected to the moving bar and a front end of the first region is inserted into the hub.

15. The catheter of claim 11, wherein the rack is positioned on an upper region between the front end of the moving bar and the rear end of the hub.

16. The catheter of claim 11, wherein the gear is fixed by being engaged with the rack and the tooth of the hub to then couple the pivot and the hub to each other.

17. The catheter of claim 11, wherein the rack is lowered from the second region to the first region while being retracted.

18. The catheter of claim 17, wherein as the rack is lowered, the gear is rotated to then be disengaged from the tooth of the hub and the pivot and the hub are separated from each other.

19. The catheter of claim 17, wherein the rack cuts off an outwardly traveling path of the needle extending from the pivot.

20. The catheter of claim 11, further comprising a needle hub enclosing the outer periphery of the moving bar and having a rear end integrally coupled to the rear end of the plug.

* * * * *